(12) United States Patent
Fang et al.

(10) Patent No.: US 11,808,672 B2
(45) Date of Patent: Nov. 7, 2023

(54) DETECTION DEVICE

(71) Applicant: Zhejiang Orient Gene Biotech Co., Ltd., Anji Huzhou (CN)

(72) Inventors: Jianqiu Fang, Anji Huzhou (CN); Siyu Lei, Anji Huzhou (CN); Lili Shen, Anji Huzhou (CN)

(73) Assignee: ZHEJIANG ORIENT GENE BIOTECH CO., LTD., Anji Huzhou (CN)

( * ) Notice: Subject to any disclaimer, the term of this patent is extended or adjusted under 35 U.S.C. 154(b) by 239 days.

(21) Appl. No.: 16/866,217

(22) Filed: May 4, 2020

(65) Prior Publication Data
US 2021/0270701 A1 Sep. 2, 2021

(30) Foreign Application Priority Data

| Mar. 2, 2020 | (CN) | 202010134242.5 |
| Mar. 2, 2020 | (CN) | 202010134256.7 |
| Mar. 2, 2020 | (CN) | 202020234643.3 |
| Mar. 2, 2020 | (CN) | 202020234667.9 |
| Mar. 2, 2020 | (CN) | 202020236601.3 |

(51) Int. Cl.
G01N 1/12 (2006.01)
G01N 33/487 (2006.01)

(52) U.S. Cl.
CPC .............. *G01N 1/12* (2013.01); *G01N 33/487* (2013.01)

(58) Field of Classification Search
CPC .............................. G01N 1/12; G01N 33/487
(Continued)

(56) References Cited

U.S. PATENT DOCUMENTS

| 6,085,920 A * | 7/2000 | Moretti | B65D 41/34 |
| | | | 215/277 |
| 2007/0092402 A1* | 4/2007 | Wu | B01L 3/502 |
| | | | 422/400 |
| 2019/0339263 A1* | 11/2019 | Lei | G01N 33/94 |

FOREIGN PATENT DOCUMENTS

CN 2271895 * 1/1998

* cited by examiner

*Primary Examiner* — John Fitzgerald
*Assistant Examiner* — Rodney T Frank
(74) *Attorney, Agent, or Firm* — NZ Carr Law Office

(57) ABSTRACT

The invention provides a detection device, comprising a fluid sample collecting chamber, the collecting chamber including an opening, a testing element is arranged in the collecting chamber, and the testing element is used to test the presence of the analyzed substance in the fluid sample; the detection device further comprises a cover body used to close the opening of the collecting chamber; wherein the cover body includes an elastic card used to engage the opening of the collecting chamber, when the cover body closes the opening of the collecting chamber, the elastic card engages the outer wall of the opening of the collecting chamber, thereby fixing the cover body on the collecting chamber. The cover body of the invention is buckled with the collecting chamber, an elastic card and a buckle structure are arranged to facilitate fastening between the cover body and the bottle body, but make it difficult to separate them apart; this can avoid leakage of a sample inside the collecting chamber; a guide structure is arranged in the cover body, so that a closing area is formed when the opening of the collecting chamber is not deliberately aligned with the elastic card in the cover body during using, the closing between the cover body and the collecting chamber can be easily achieved, thereby improving the testing efficiency.

19 Claims, 10 Drawing Sheets

Figure 1:
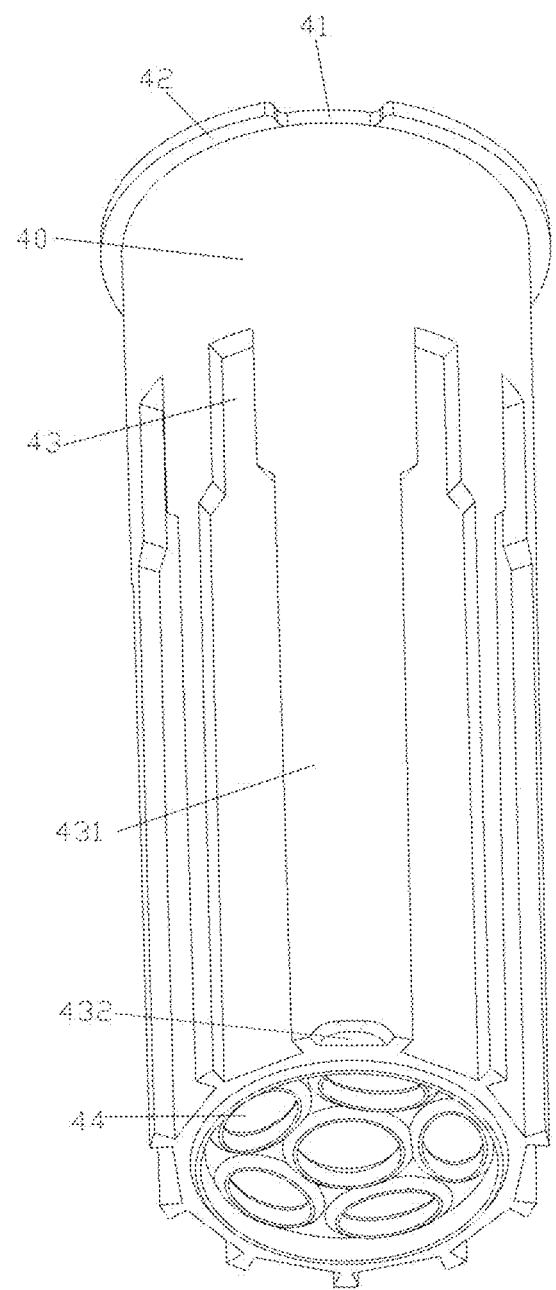

(58) Field of Classification Search
USPC .................................................... 73/864.51
See application file for complete search history.

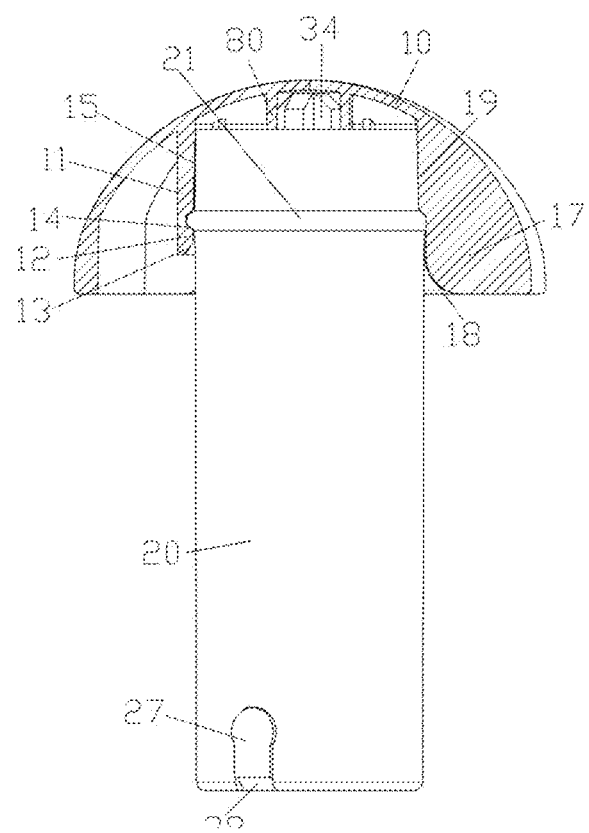
FIG. 7A
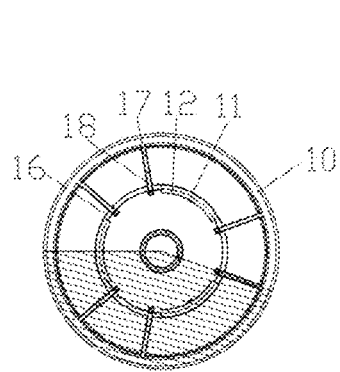 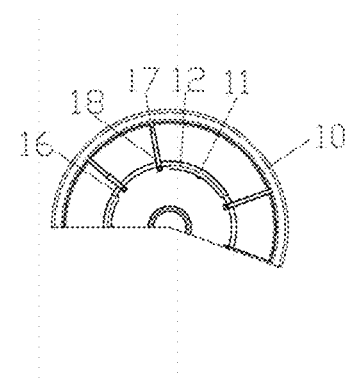
FIG. 7B          FIG. 7C

DETECTION DEVICE

CROSS REFERENCE

The present application claims the priority from China Patent Application Nos. 202020236601.3, 202010134242.5, 202020234667.9, 202010134256.7, 02020234643.3, filed on Mar. 2, 2020. The entire contents of these applications including all tables, diagrams and claims are incorporated hereby as reference.

TECHNICAL FIELD

The present invention relates to the field of vitro rapid detection technology, in particular to a device for collecting and detecting the analyzed substance in a fluid sample in the field of rapid diagnosis, for example, a urine and saliva collection and detection device.

BACKGROUND

The following background art information is only a general introduction of the background and will not constitute any restrictions on the present invention.

Currently, the device used to detect the presence of the analyzed substance in the detected sample is widely used in hospitals and households. These rapid diagnostic devices comprise one or more test strips, including pregnancy test, drug abuse detection, etc. The quick diagnosis detection device is very convenient, the device can show the detection result on the test strips in one minute, or ten minutes at most.

Drug detection is widely used in drug control authorities, Public Security Bureaus, drug treatment centers, physical examination centers, national conscription physical examination centers, etc. There are various kinds of drug detection, and the detection is very frequent. Some detections need sample collection and require a professional testing agency or laboratory for detection. Some detections must be completed on the spot in a timely manner, for example, people who drive after taking drugs ("drugged driving" for short) need to be tested on the spot so that the test result can be obtained at once. For drug detection, the sample can be urine, sweat, hair and saliva.

For convenient collection of sample, the detection of saliva samples is gradually accepted and welcomed by the testing agency or the testing personnel. Various sample collecting and testing devices for clinical or household purpose have been seen and described in some literatures. For example, U.S. Pat. No. 5,376,337 discloses a saliva sample collector, wherein a filter paper is used to collect saliva from a subject's mouth and transfer the saliva to an indicator reagent. U.S. Pat. Nos. 5,576,009 and 5,352,410 disclose an injector-type fluid sample collector separately.

A drug detection device is also described in U.S. Pat. No. 7,927,562, wherein the cover body of the device fits a collection device with a test strip in the form of threads. The threaded seal is still difficult to operate, especially when there are many samples to be tested although it can achieve the purpose of sealing the collecting chamber, operation by way of rotation is not convenient and inefficient. In another embodiment, another drug detection device is also described in the U.S. Pat. No. 9,462,998, wherein a raised thin sheet is arranged on the cover body, the thin sheet contacts the inner wall of the collecting chamber when the cover body is inserted in the cavity, so that the cover body can be kept on the collecting chamber easily, thereby limiting its position. A thin sheet structure is arranged on the device, this is not easy to realize in the actual product design and production, because the mold production of plastic parts seems difficult.

This requires an improvement on the existing traditional detection devices to provide a device for collecting a sample and testing the sample of the analyzed substances in a fluid sample in a simpler way.

SUMMARY OF THE INVENTION

The purpose of the present invention is to provide a detection device to solve the problems in the above background art.

The technical solution used to achieve the above mentioned purpose is a detection device, wherein the detection device comprises a fluid sample collecting chamber, the collecting chamber including an opening, a testing element is arranged in the collecting chamber, and the testing element is used to test the presence of the analyzed substance in the fluid sample; the detection device further comprises a cover body used to close the opening of the collecting chamber; wherein the cover body includes an elastic card used to engage with the opening of the collecting chamber, when the cover body closes the opening of the collecting chamber, the elastic card engages with the outer wall of the opening of the collecting chamber, thereby fixing the cover body on the collecting chamber. In some embodiments, the elastic card engages on the outer wall near the opening of the collecting chamber, to fix the cover body on the collecting chamber depending on the elastic liner.

In some embodiments, the elastic card includes a buckle structure, an outer wall of the collecting chamber includes a convex structure, and the buckle structure engages the convex structure when the cover body closes the opening of the collecting chamber, so as to achieve the fitting between the cover body and the collecting chamber. The clamping mentioned here refers to fitting between the buckle structure and the convex structure on the cavity, similar like the way of snap-fitting.

In some embodiments, the buckle structure comprises a lower buckle surface and an upper buckle surface, and the angle formed by the lower buckle surface and the horizontal plane is larger than that formed by the upper surface and the horizontal plane. Thus, the slope of the lower buckle surface is larger than that of the upper buckle surface, when the cover body fits with the collecting chamber (the collecting chamber is inserted in the buckle structure of the cover body or the cover body and the collecting chamber fit in the way of relatively inserting in each other); due to the large slope of the lower buckle surface, the contact between the lower buckle surface and the convex structure enables the elastic deformation of the elastic card to be relatively easier, and the upper buckle surface can fit with the convex structure by gently pushing. When the cover body and the collecting chamber have to be separated, as the slope of the upper buckle surface is small, the contact between the upper buckle surface and the convex structure enables the elastic deformation of the elastic card to be relatively difficult. This can be demonstrated by the operator's feeling during separation: it can only be separated by a great force. In other words, for the elastic card, the situation is that the lower buckle surface is at a slowly rising angle, the slope of the lower buckle surface is relatively larger than that of the upper buckle surface, and the upper buckle surface is horizontal or slightly forms an acute angle with the horizontal position.

In some embodiments, the convex structure further comprises an upper buckle surface and a lower buckle surface, wherein the angle formed by the lower buckle surface and the horizontal plane is smaller than that formed by the upper buckle surface and the horizontal plane, or the slope of the lower buckle is larger than that of the upper buckle. In other words, for the convex structure, the situation is that the upper buckle surface is at a slowly rising angle, the slope of the upper buckle surface is relatively larger than that of the lower buckle surface, the lower buckle surface is horizontal or slightly forms an acute angle with the horizontal position. The upper buckle of the convex structure contacts the lower buckle of the elastic card, the two surfaces slide relatively, and the convex structure can be pushed into the upper buckle surface of the elastic card by a small force.

In some embodiments, at least two elastic cards are arranged in the cover body, as a preferred technical solution, the cover body presents a half hollow sphere shape, the bottle body is cylindrical, three elastic cards are arranged in a circular array with the central axis of the cover body as the center, under the effect of an external force, the elastic cards may get away from the central axis side of the cover body, thereby leading to elastic deformation.

In some embodiments, the elastic cards are arc-shaped, the center of the circular arc is on the central axis of the cover body, and the arc-shaped elastic card can facilitate the elastic card to restore to its original state after deformation.

In some embodiments, a circular ring is arranged in the cover body, and the circular ring is connected to all the elastic cards, the circular ring can strengthen the connection between the cover body and the elastic lamp so that the elastic card may not be easily fractured; meanwhile, the circular ring can prevent leakage of liquid sample in the collecting chamber, thereby limiting the position of the collecting chamber in the cover body better.

In further embodiments, a limiting strip is arranged on the elastic cards and the limiting strip extends into the circular ring, when the cover body and the collecting chamber are closed, the limiting strip and the buckle structure can limit the position of the convex structure from the upper and lower sides, so that the cover body can be stably kept on the bottle body; the limiting strip extends into the circular ring and always keep in contact with the opening of the collecting chamber, thus to ensure the upper end of the bottle body is inserted in the circular ring.

Further, a guide structure is arranged in the cover body, the guide structure is located between the two adjacent elastic cards; at least two guide structures are arranged as at least two elastic cards are arranged inside the cover body, the guide structure has a guide effect in closing the cover body and the collecting chamber, it is not necessary to align the bottle mouth with the buckle area formed by the inner elastic card of the cover body when using to easily achieve fitting between the cover body and the collecting chamber.

Further, the guide structure is in fan blade shape, the guide blade is connected to the bottom part of the cover body and the circular ring, a round corner is arranged at the edge of the guide structure or the edge is in arc-shaped, when the bottle mouth is not aligned with the fitting area in the cover body, the upper end of the bottle comes into contact with the blade, it may enter the fitting area under the guidance of the round corner or the arc-shaped structure to facilitate accurate operation, thereby avoiding offset.

Further, a convex support is arranged on the guide blade, the height of the lower end of the convex support is the same as that of the lower end of the limiting strip, and this can limit the position of the convex structure; in addition, after the guide blade is connected to the bottom part and the circular ring of the cover body, the overall strength of the cover body can be strengthened to some extent, as a preferred technical solution, there are six guide blades and the guide blades are arranged respectively between the adjacent elastic cards in a circular array.

In some preferred embodiments, a carrier is also arranged in the collecting chamber, a plurality of card slots are arranged on the carrier, and a testing element is arranged on each card slot. In some embodiments, the carrier and the collecting chamber are matched in a special way, so that the carrier is inserted in the collecting chamber in a unique direction. In some embodiments, when the collecting chamber is a cylinder, the upper end of the carrier folds outward to form a convex platform, a concave platform is arranged in the collecting chamber, and the convex platform can hold or locate on the concave platform. After the concave platform is erected on the convex platform, the carrier cannot go to move forward. This can limit the longitudinal position of the collecting chamber on the carrier. In some embodiments, a limiting buckle is arranged on the concave platform so that the convex platform may not easily fall off after it is erected on the concave platform. This is to ensure the carrier should not drop out easily after being installed into the collecting chamber 22. In some preferred embodiments, a notch 41 is arranged on the convex platform, a bulge matching the notch is arranged on the concave platform, and the notch and the bulge are both used to determine the installation direction of the carrier on the collecting chamber. Therefore, the carrier can only be inserted in the collecting chamber in a single direction, meanwhile, this can limit the inserting direction of the carrier, and ensure the carrier has the only position relation in the collecting chamber.

In some embodiments, the grooves on the carrier are arranged on the outer surface of the carrier in the form of a circular array, wherein no opening is arranged at one of the groove positions, thus to form a blank area. The bulge and notch can limit the position of the carrier in the collecting chamber, so the blank area of the carrier is at the fixed position in the collecting chamber. In some embodiments, a sampling hole in correspondence to the blank area is arranged in the collecting chamber near the bottom position, the sampling hole 26 is used for second sampling and testing of a liquid sample. In some embodiments, a sample area is also arranged on the carrier, the sample area 2 is in a sunken form, the area is fitted with the bottom part of the collecting chamber to form a sample space, and a sampling hole is arranged on the sample space. The purpose of the arrangements is as follows: no test strip is arranged in the blank area if there is no groove in the blank area, this can prevent the sampling hole from being blocked by the sample application area of the test strip or the testing element; meanwhile, the sample is directly extracted from the sampling hole of the bottle, thereby avoiding pollution of the sample during second sampling.

To sum up, the present invention has the following beneficial effects that a detection device of the present invention is characterized in that, the cover body and the collecting chamber are closed, the arrangement of elastic cards and the buckle structure enables the cover body and the bottle to be fitted up easily but difficult to separate; the circular ring on the cover body wraps the collecting chamber up so that the sample in the collecting chamber does not leak, and the bottle is prevented from swinging; the guide structure in the cover body, can easily achieve the closing between the cover body and the collecting chamber when the opening of the collecting chamber is not deliberately aligned with the elastic card in the cover body during using; a plurality of grooves are arranged on the outer surface of the carrier and are used for installing different testing elements, so as to exert the function of various testing at one time; the bottom part of the bottom is convex upward to distribute the liquid sample in the collecting chamber in all directions and come into contact with the testing element, so that the sampling quantity of the liquid sample can be reduced without affecting the detection results; the detection device presents a mushroom shape, cute and artistic, and the device can remove the fear of the subject, more easily to be accepted.

DETAILS OF DRAWINGS

Figure 2:
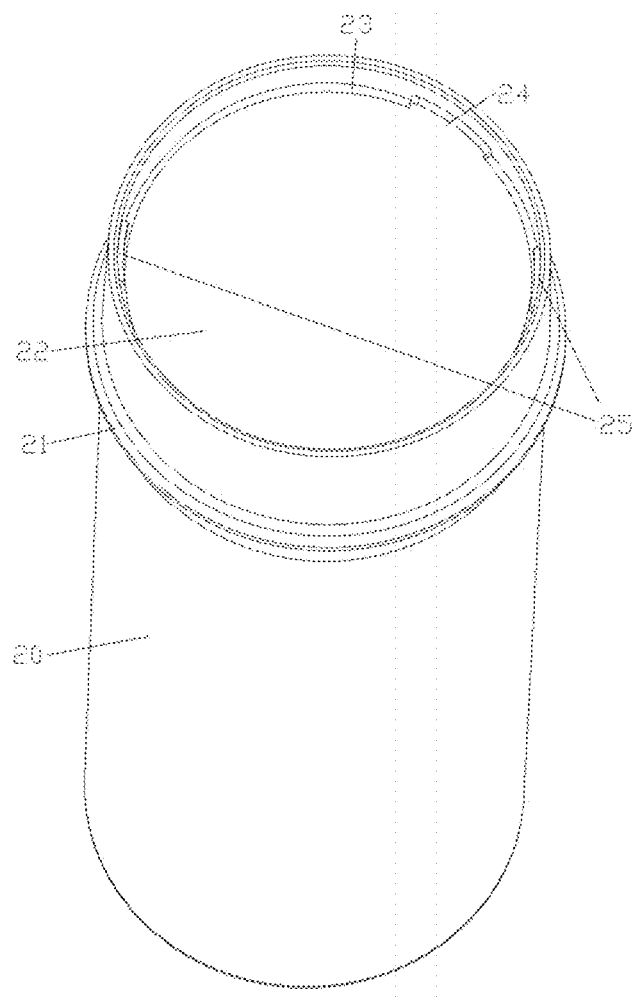
Figure 3:
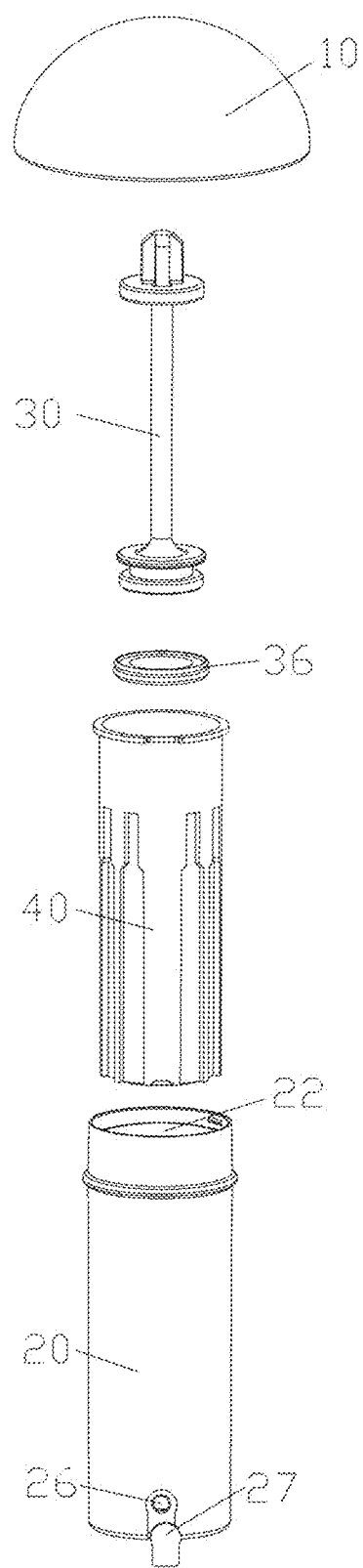
Figure 4:
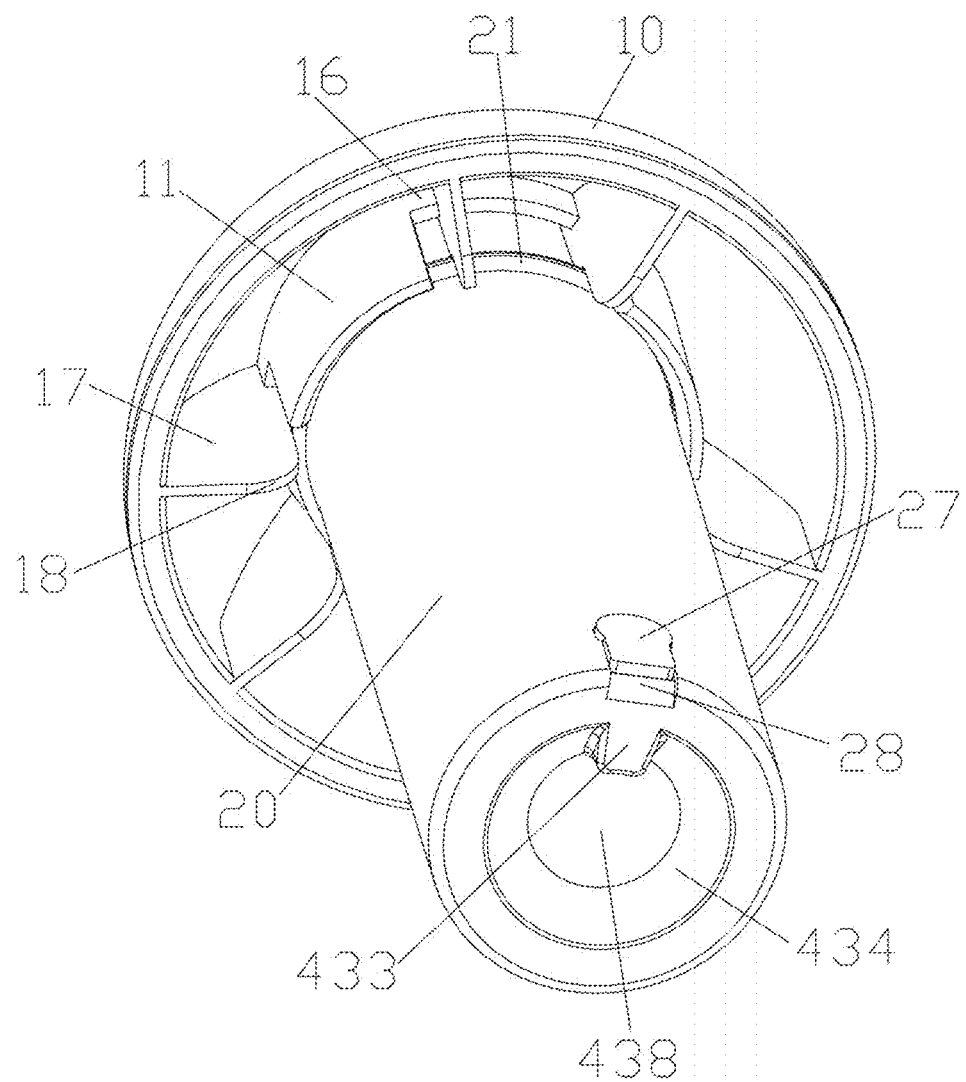
Figure 5:
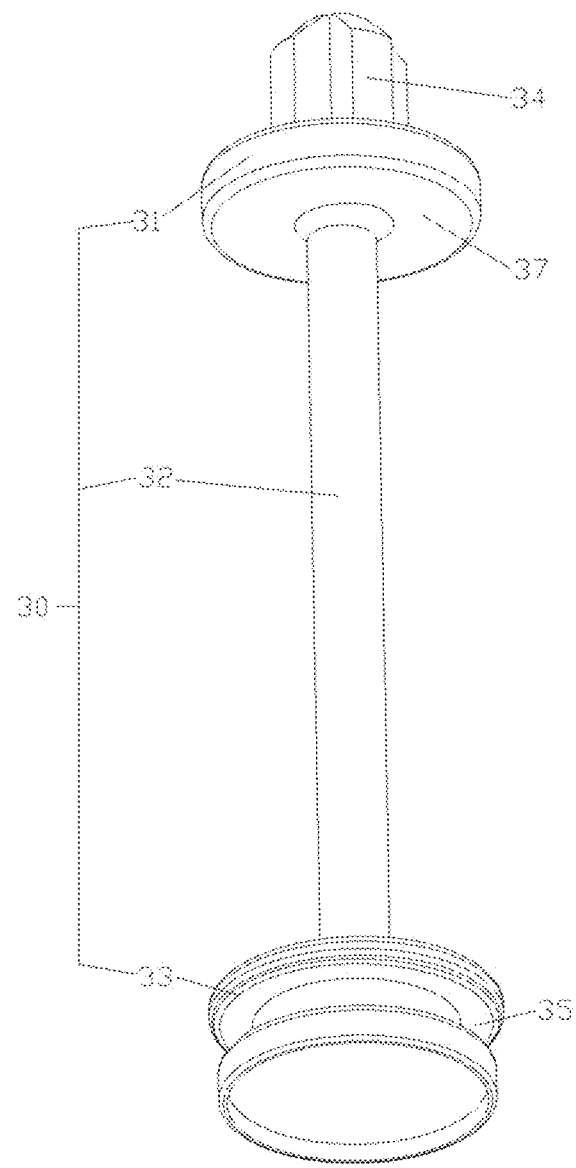
Figure 6:
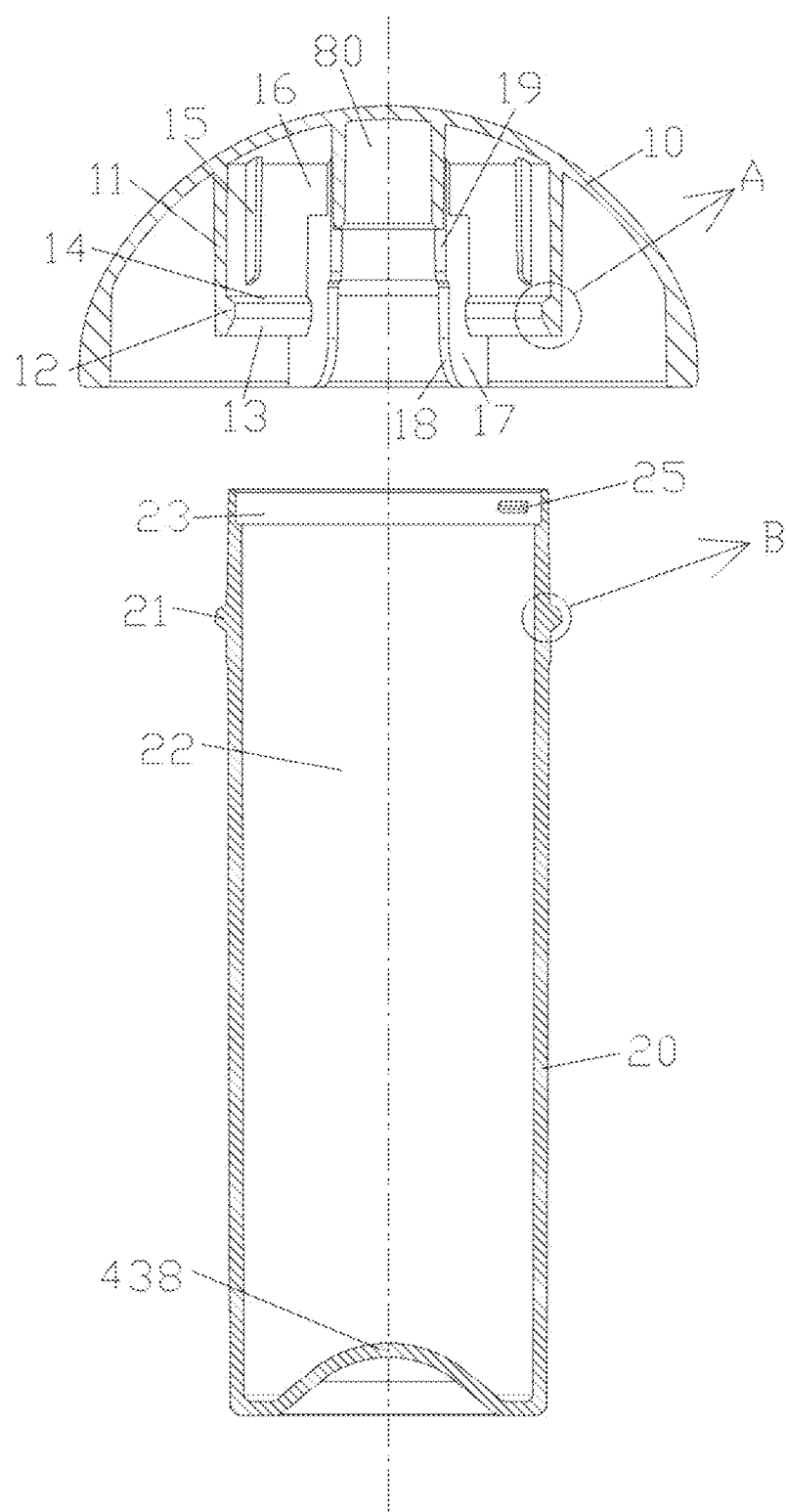
Figure 8:
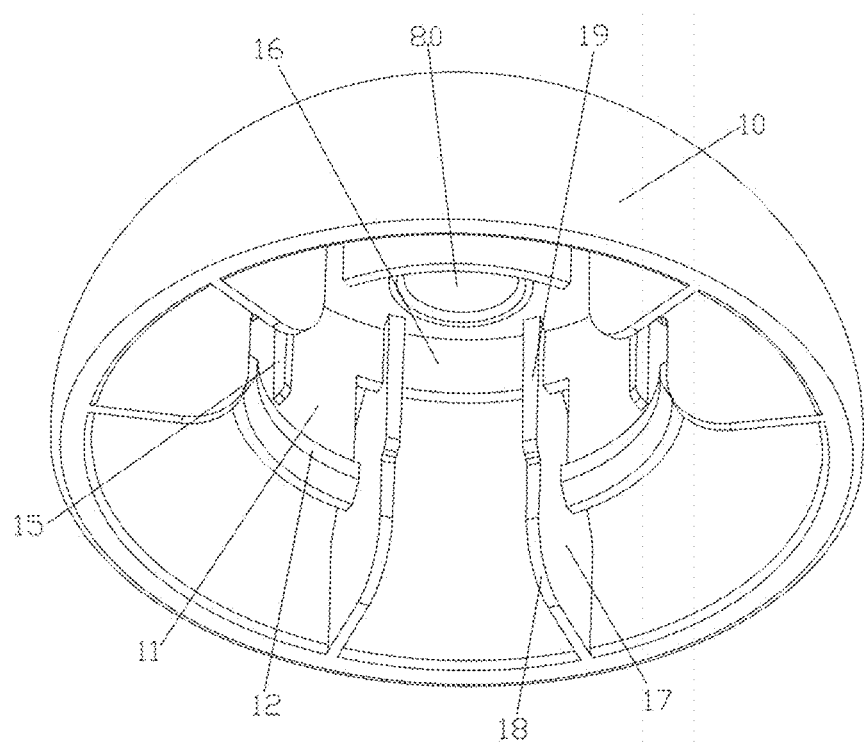
Figure 9:
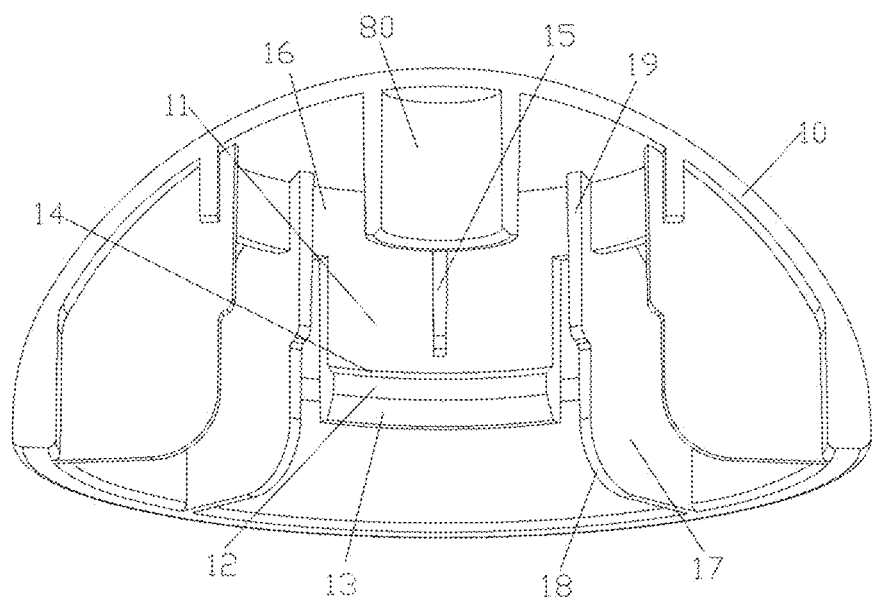
Figure 10:
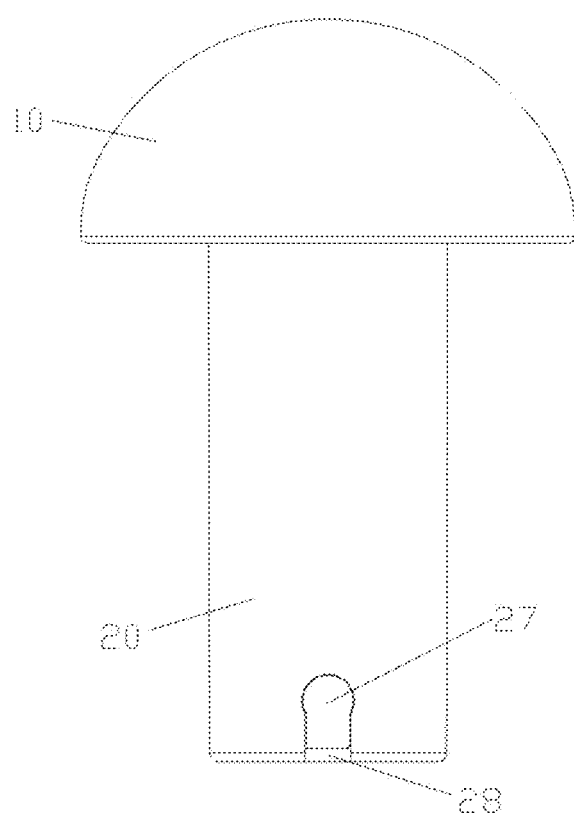
Figure 11:
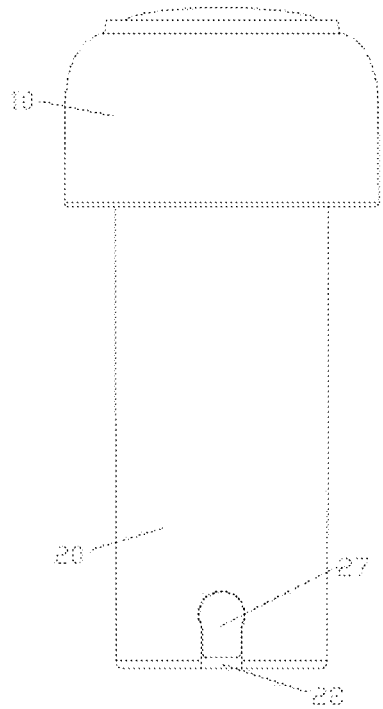
Figure 12:
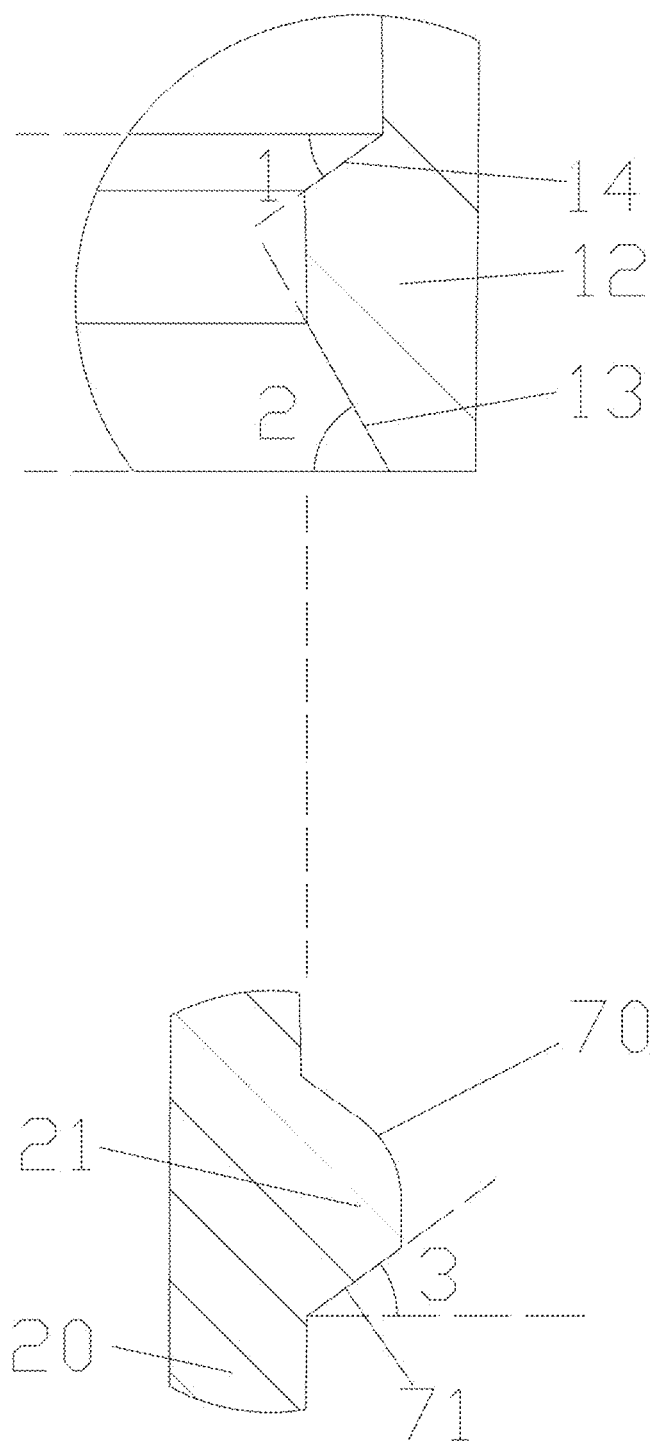

FIG. 1 depicts a structure diagram of the carrier;
FIG. 2 depicts a structure diagram of the bottle;
FIG. 3 depicts an exploded view of the detection device;
FIG. 4 depicts a structure diagram of the bottom part of the detection device;
FIG. 5 depicts a structure diagram of the sample collector;
FIG. 6 depicts a structure diagram of fitting between the cover body and the collecting chamber;
FIGS. 7A-7C depict an overall structure diagram of the device when the cover body is opened;
FIG. 8 depicts a structure diagram of the cover body;
FIG. 9 depicts a half-section diagram of the cover body;
FIG. 10 depicts an overall structure diagram of a detection device
FIG. 11 depicts an overall structure diagram of another detection device
FIG. 12 depicts local magnification diagram of "A" and "B" areas in FIG. 6.

DETAILED DESCRIPTION

The following is a further explanation of the structures involved in the invention or of the technical terms used, unless specifically specified, they will be understood and interpreted in accordance with the general terms in use in the field.

Test

A test is to conduct experiment or test to determine the presence of a substance or material, for example, but not limited to, chemicals, organic compounds, inorganic compounds, metabolic products, drugs or drug metabolites, organic tissue or metabolites of organic tissues, nucleic acids, proteins, or polymers. In addition, a test indicates the quantity of a substance or material tested. Furthermore, test also means immunity test, chemical test, enzyme test, etc.

Specimen

Samples that can be detected by the detection device of the present invention or the sample that can be collected include biological fluid (such as a case fluid or a clinical sample). Liquid sample or liquid specimen, or fluid specimen or fluid sample can be derived from solid or semi-solid samples, including feces, biological tissues and food samples. The solid or semi-solid samples can be converted into the liquid samples by any suitable method, such as mixing, mashing, macerating, incubating, dissolving or utilizing enzymolysis to digest the solid samples in suitable solutions (such as water, a phosphate solution or other buffer solutions). "Biological samples" include animal, plant and food samples, for example, including urine, saliva, blood and its components, spinal fluid, vaginal secretions, sperms, feces, sweat, secretions, tissues, organs, tumors, cultures of the tissues and the organs, cell cultures and media derived from humans or animals. The preferred biological sample is urine; and the preferred biological sample can also be saliva.

The food samples include food processing substances, final products, meat, cheese, wine, milk and drinking water. The plant samples include any plants, plant tissues, plant cell cultures and media. "Environmental samples" are derived from environment (for example, the liquid samples from lakes or other water bodies, sewage samples, soil samples, groundwater, seawater and waste liquid samples). The environmental samples may also include sewage or other wastewater.

A suitable detection element or testing element of the present invention can be used to detect any analyte. The present invention is preferably utilized to detect small drug molecules in the saliva and the urine. Of course, the collection device of the present invention can collect any of the above samples, either solid or liquid at the very beginning, as long as the liquid or the liquid specimen can be absorbed by an absorber element. The absorption element herein are generally made of absorbent materials (dry at the beginning), and can absorb liquid specimen or fluid specimen through the capillary or other characteristics of the absorber element. The absorber material can be any material that can absorb liquid materials, such as sponge, filter paper, polyester fiber, gel, non-woven fabrics, cotton, polyester thin film, yarn, etc. Of course, the absorber element is not necessarily made of absorbent materials, and it can be made of non-absorbent materials. However, there are holes, threads and holes on the absorber elements so the specimen can be absorbed on the above structures, the specimens are generally solid or semi-solid samples and are filled between threads, holes, or holes.

Downstream and Upstream

Downstream or upstream is defined by the direction in which the liquid flows, and generally liquid flows from upstream to downstream. Liquid in the downstream region or received from the upstream region: the liquid can also flow along the upstream region to the downstream region. It is generally defined by the direction in which the liquid flows. For example, in some materials where capillary force is used to make the liquid flow, the liquid can flow by gravity in the opposite direction to gravity. In this case, the upstream and downstream of the liquid are also defined by the direction in which the liquid flows.

Gas Communication or Liquid Communication

Gas communication or liquid communication means liquid or gas can flow from one place to another, and may pass by physical structures that plays a role of guidance during the flow process. The so-called passing by the physical structures generally means the liquid pass by the surface of the physical structure, or the internal space of the structure so that it passively or actively flows to another place; passive flow is a flow caused by application of an external force, for example, the flow under capillary action. The flow here can be liquid flow or gas flow, and it can be passive flow due to its own effect (gravity or pressure). The communication here does not necessarily mean that a liquid or gas is required, but indicates the connection relationship or state between two objects only in some cases. If there is a liquid, it can flow from one object to the other. Here, it refers to the state where two objects are connected; on the contrary, if there is no liquid or gas communication between the two objects, and there is liquid in or on an object, the liquid cannot flow into or on the other object, this is non-communication, non-liquid or gas-communicated state.

Testing Element

The so-called "testing element" herein refers to the element that can detect whether a specimen or a sample contains the analyte of interest. This detection can be based on any of the technical principles, such as immunological, chemical, electrical, optical, molecular, nucleic acid, physical principles. The testing element can use a lateral flow test strip, and the test strip can detect a variety of analytes. Of course, other suitable testing elements can also be applied in the present invention.

Various testing elements can be combined and used in the present invention. One of the forms is a test strip. A test strip used to analyze the analyte in a sample (such as a drug or a metabolite that indicates a medical condition), can be in various forms, such as immunoassay or chemical analysis. Test paper can adopt the analysis mode of a non-competition law or a competition law. The test paper generally includes an absorbent material with sample feeding area, a reagent area and a test area. The sample is added to the sample feeding area, and flows to the reagent area through capillary action. In the reagent area, if an analyte is present, the sample will bind with the reagent. Then, the sample continues to flow to the detection area. Other reagents, such as molecules specifically bonded with the analyst, are fixed in the detection area. The reagents react with the analyze (if any) in the sample and bind with the analyze in the area or bind with one of the reagents in the reagent area. The marker used to show a detection signal exists in a reagent area or a separated marker area.

The typical non-competitive analysis model is that if the sample contains the analyte, a signal can be generated; if the sample does not contain the analyte, a signal may not be generated. In competition law, if the analyte does not exist in the sample, a signal may be generated; if the analyte exists, a signal may not be generated.

The testing element may be a kind of test paper, and it can also be an absorbent material or a non-absorbent material. The test paper can include various materials for transferring liquid sample. Wherein, the material of one kind of the test paper may be covered over another material, for example a filter paper covered over a nitrocellulose membrane. One area of the test paper can use one or more materials, and the other area can use one or more of the other different materials. The test paper can be attached to a support or a hard surface to improve the strength to hold the test paper.

The analyte is detected by a signal generating system, fixing one or more compositions of the signal generating system in the analyte detection area of the test paper by using one or more enzymes that react specifically with the analyte, and or the method of fixing the specific binding substance on the test paper as described above. The substance that produces a signal may be in the feeding area, the reagent area, or the detection area, or on the entire test paper, and the substance may be filled with one or more of the materials on the test paper. Adding a solution containing a signal to the surface of the test paper or to immerse one or more of the materials of the test paper in a solution containing a signal. Drying up the test paper containing the signal solution.

All areas of the test paper can be arranged in the following ways: a sample feeding area, a reagent area, a detection area, a control area, an area for determining adulteration in the sample and a liquid sample absorption area. The control area is located behind the detection area. All areas can be arranged on a piece of test paper containing only one material. However, different materials are used in different areas. All areas can be in direct contact with the liquid sample, or different areas can be arranged according to the flow direction of the liquid sample, and the rear end of each area is connected and to the front end of another area and overlapped with each other. The materials used can be excellent water-absorbent materials, such as filter paper, glass fiber or nitrocellulose membrane. The test paper can also be used in other forms.

The commonly used reagent strip is a nitrocellulose membrane reagent strip. The detection area includes a nitrocellulose membrane, and specific binding molecules are fixed on the nitrocellulose membrane to indicate the detection result; it can also be a cellulose acetate membrane or a nylon membrane. For example, the test strip or device containing a test strip of the following patents: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620; and 6,403,383. The test strips disclosed in the above patent documents and the similar devices with a test strip can be applied to the testing element or testing device of the invention for detecting analyte, for example the detection of a divided substance from the sample.

The test strips applied to the present invention can be commonly referred to as a lateral flow test strip, and the specific structure and detection principle of the detection reagent strips are known to general technicians in the field in the prior art. An ordinary test strip comprises a sample collection area or a sample feeding area, a marker area, a detection area and a water absorption area, wherein the sample collection area includes a sample receiving pad, the marker area includes a marking pad, the water absorption area can include a water-absorbing pad, the detection area includes the necessary chemical substances that can detect the presence of an analyte, such as an immunological reagent or an enzyme chemical reagent. The commonly used test strip is a nitrocellulose membrane strip, that is, the detection area includes a nitrocellulose membrane, and specific binding molecules are fixed on the nitrocellulose membrane to indicate a detection result; it can also be a cellulose acetate membrane or a nylon membrane, etc. Also, the detection area can also include a detection result control area in the downstream, generally, the control area and the detection area appear in the form of horizontal lines, which are called a detection line or a control line. The test strip is a conventional reagent strip, and it can also be other types of reagent strips that detect by the capillary action. Furthermore, a test strip generally includes a dry chemical reagent component, such as a fixed antibody or any other reagent, when encountering a liquid, the liquid flows along the reagent strip under the capillary action, and the dry reagent component is dissolved in the liquid during the flow process, reacts with the dry reagent of the area in the next area, thus to carry out the necessary detection. The liquid flows depending on the capillary action. All of the above can be applied to the detection device of the present invention, or arranged in a testing chamber to get contact with a liquid sample, or used to detect the presence or amount of an analyte in a liquid sample that enters the testing chamber.

In addition to testing the presence of an analyte in the liquid sample by using the above test strip or lateral flow test strip to contact with a liquid sample. In some preferred embodiments, the testing element can also be arranged on some carriers, as shown in FIG. 1, for example, on some carriers 40, wherein there are a plurality of grooves 43 on the carriers, and the testing element is located in the groove 43. In some embodiments, the carrier 40 includes a groove area where a testing element is arranged, and a plurality of grooves are arranged in the area, a test strip is arranged in a groove, and each test strip can detect an analyte. As shown in FIG. 1-3, the carrier 40 matches with the collecting chamber 22, when the collecting chamber 22 is a cylinder, a circular carrier can be placed in the collecting chamber 22, and a plurality of grooves are arranged on the outer surface of the carrier, a testing element is placed in the groove, the testing element can be a test strip, the opening on the upper side of the groove is small and mainly have the function of fixing the test strip, the opening on the lower side of the groove is large, so as facilitate the test strip to absorb the liquid sample upward. In some embodiments, after the testing element is arranged in the groove of the carrier, a transparent thin film is covered on the carrier to seal the groove area of the carrier, and the transparent thin film can make it easy to observe the test result on the final detection area. The transparent thin film can also be a transparent plastic sheet, which is only transparent in the test area.

Generally, the test strip includes a sample feeding area, a marker area, and a detection area; wherein when placing the test strip, the sample feeding area is placed near the bottom of the carrier, and then get out of the groove slightly, for example 2-3 mm, a partial sample feeding area is used to absorb a fluid sample flowing into the bottom of the collecting chamber. Generally, the sample feeding area is located at upstream of the marker area, and the marker area is located at upstream of the detection area.

Carrier and Collecting Chamber

A collecting chamber is a place for containing samples, as shown in FIG. 1-3, a collecting chamber 22 is arranged on the bottle body 20, the collecting chamber 22 includes an opening on the upper side of the bottle body 20, and a carrier 40 is inserted into the collecting chamber 22 from the opening on the upper side of the bottle body 20. In some embodiments, the carrier 40 and the collecting chamber 22 are specifically matched. The above matching method allows the carrier to have a definite and unique directional location after being inserted into the collecting chamber. Specifically, when the collecting chamber 22 is a cylinder, a cylindrical carrier can be placed in the collecting chamber 22, the upper end of the carrier 40 folds outward to form a convex platform 42, a concave platform 23 is arranged in the collecting chamber 22, and the convex platform 42 can hold or locate on the concave platform 23, that means, after the concave platform 42 is erected on the convex platform 23, the carrier 40 cannot go to move forward. This can limit the longitudinal position of the collecting chamber on the carrier. A limiting buckle 25 is arranged on the concave platform 23, so that the convex platform 42 may not easily fall off after it is erected on the concave platform 23, the carrier 40 may not drop out easily after being installed into the collecting chamber 22. In some preferred embodiments, a notch 41 is arranged on the convex platform 42, a bulge 24 matching the notch 41 is arranged on the concave platform 23, and the notch 41 and the bulge 24 are both used to determine the installation direction of the carrier 40 on the collecting chamber 22. Therefore, the carrier can only be inserted in the collecting chamber in a single direction, meanwhile, this can limit the inserting direction of the carrier, and ensure the carrier has the only position relation in the collecting chamber. The only position relation is related to the second sampling locations described below.

Except being used for installing the above testing element, the carrier also has the function of squeezing the sample collector and feeding the sample into the collecting chamber, as shown in FIGS. 1-3, a carrier 40 is barrel-shaped and is provided with an opening on the upper side, a sample collector 30 is inserted into the carrier 40 along the opening on the upper side of the carrier 40 and is squeezed with the bottom part of the carrier 40; the sample is extruded from the sample collector and enters the space inside the carrier 40, The bottom of the carrier 40 is provided with a plurality of through-holes 44 are arranged at the bottom part of the carrier 40 to connect the space inside the carrier 40 with a collecting chamber 22, test paper is loaded in the groove 43, the lower end of the test paper is contacted with the bottom of the collecting chamber 22, or is very close to the bottom of the collecting chamber 22, the sample inside the carrier 40 flows into the collecting chamber 22 through the through-hole 44 and contacts with the test paper, thus to start the detection.

The grooves 43 are arranged on the outer surface of the carrier 40 in the form of a circular array, wherein no opening is arranged at one of the groove positions, thus to form a blank area 431, as shown in FIG. 1, the bulge 24 and notch 41 can limit the position of the carrier 40 in the bottle body 20, so the blank area 431 of the carrier 40 is at the fixed position in the bottle body 20, as shown in FIG. 3, a sampling hole 26 in correspondence to the blank area 431 is arranged on the bottle body 20 near the bottom position, and the sampling hole 26 is used for second sampling and testing of a liquid sample. A sample area 432 is also arranged on the carrier 40, the sample area 432 is in a sunken form, the area is fitted with the bottom part of the collecting chamber 22 to form a sample space 433, and a sampling hole 26 is arranged on the sample space 433. The purpose of the arrangements is as follows: no test strip is arranged in the blank area if there is no groove 43 in the blank area 431, this can prevent the sampling hole 26 from being blocked by the sample application area of the test strip or the testing element; meanwhile, the sample is directly extracted from the sampling hole 26 of the bottle body 20, thereby avoiding pollution of the sample during second sampling. The reason is as shown in FIG. 4, the sample space 433 has a certain isolation effect on the liquid sample from other locations in the collecting chamber 22 (for example, the area 434 located the test strip), The liquid samples in area 434 need to contact with the test strip, while the samples in the sample space 433 avoid contact with the test strip because there is no test strip in this location, the liquid sample in area 434 needs to be in contact with the test strip, while the sample in the sample space 433 does not have a test strip at the position, so the contact with the test strip is avoided; when a second sampling is conducted for analysis and confirmation, the sample in the sample space 433 may not be contaminated by the test strip. In some embodiments, a sampling hole 26 is provided with a sampling plug 27, as shown in FIG. 4, wherein the sampling plug 27 can prevent a liquid sample from flowing out of the sampling hole 26. In some preferred embodiments, a chute 28 is arranged on the bottom of the bottle body 20 at the installation position of the sample plug 27, and the chute 28 can facilitate an inspector to remove the sampling plug 27.

The bottom of the bottle body 20 is a convex 438 upward to distribute the liquid sample in the collecting chamber 22 in all directions and come into contact with the testing element, so that the sampling quantity of the liquid sample can be reduced without affecting the detection results.

Analyte

The embodiments of using the analytes involved in the present invention include some small molecular substances, and the small molecular substances include drugs (e.g., drug abuse). "Drug of abuse" (DOA) refers to use of drugs for non-medical purposes (usually paralyzing nerves). Abuse of these drugs can lead to physical and mental damage, causing dependence, addiction and/or death. Examples of DOA include cocaine; amphetamine (AMP) (such as black beauty, white amphetamine tablets, dexamphetamine, dextroamphetamine tablets and Beans); methamphetamine (MET) (crank, meth, crystal and speed); barbiturate (BAR) (such as Valium□, Roche Pharmaceuticals, Nutley and New Jersey); sedatives (i.e. sleeping aids); lysergic acid diethylamide (LSD); inhibitors (downers, goofballs, barbs, blue devils, yellow jackets and methaqualone); tricyclic antidepressants (TCA, i.e. imipramine, amitriptyline and doxepin); methylenedioxy-methamphetamine (MDMA); phencyclidine (PCP); tetrahydrocannabinol (THC, pot, dope, hash, weed, etc.); opiate (i.e. morphine (MOP) or opium, cocaine (COC), heroin and hydroxycodeinone); and antianxietics and sedative hypnotics, wherein antianxietics are a class of drugs mainly used for reducing anxiety, tension and fear, stabilizing mood and having hypnotic and sedative effects, including benzodiazepines (BZO), atypical BZ, fusion diazepines NB23C, benzodiazepines, BZ receptor ligands, ring opening BZ, diphenylmethane derivatives, piperazine carboxylates, piperidine carboxylates, quinazolinones, thiazines and thiazole derivatives, other heterocyclics, imidazole sedatives/paregorics (such as oxycodone (OXY) and methadone (MTD)), propylene glycol derivatives-carbamates, aliphatic compounds, anthracene derivatives, etc. The detection device of the present invention can also be used for detecting drugs that belong to medical use but are prone to overdose, such as tricyclic antidepressants (imipramine or the like) and acetaminophen. After being absorbed by the human body, these drugs will be decomposed into small molecule substances which are present in body fluids such as blood, urine, saliva, sweat or part of the body fluids.

For example, the analytes detected by the present invention includes but not limited to, creatinine, bilirubin, nitrite, protein (non-specific), hormone (e.g. human chorionic gonadotropin, progesterone hormone, follicle stimulating hormone, etc.), blood, white blood cell, sugar, heavy metals or toxins, bacterial substance (e.g. proteins or sugars against specific bacteria, such as *Escherichia coli* 0157: H7, staphylococci, *salmonella, clostridium, campylobacter, L. monocytogenes, vibrio*, or cactus) and substances related to physical characteristics in urine sample, such as pH and specific gravity. Any other clinical chemical analysis of a urine can be detected by combination of a lateral cross-flow detection method and the device of the invention.

Flow of a Liquid

The flow of a liquid normally refers to the flow from one place to another. Generally, the flow of a liquid in nature mostly flows from high to low by the action of gravity; the flow here also depends on an external force, i.e. flow under the actions of an external gravity, so it can be called a flow under natural gravity. In addition to gravity, the flow of a liquid can also overcome the action of gravity, so that the flow can be from low to high. For example, a liquid is extracted or compressed, or a liquid receives a pressure and then flows from low to high, or the flow is caused by the effect of the pressure or the gravity of the liquid itself. For example, a liquid sample in the carrier 40 enters the collecting chamber 22 through a through-hole 44 at the bottom of the carrier 40 under the action of gravity, The liquid sample contacts the lower end of a test strip on the carrier 40 and flows from low to high under a capillary force.

Sample Collector

A sample collector is used to collect samples, as shown in FIG. 5, the sample collector 30 comprises a connecting end 31, a rod body 32, and a sampling end 33, wherein the connecting end 31 includes a cross connector 34 and a pressing platform 37, the end of the cross connector 34 gradually becomes sharper to facilitate the connection of the cross connector 34 with a cover body, the sampling end 33 is used to connect an absorption element, the absorption element can be a non-toxic sponge with strong water absorption, and the absorption element and the sampling end 33 can be bonded by special cement, an annular groove 35 is arranged on the sampling end 33, and a seal ring 36 is installed in the annular groove 35, when the sample collector 30 is inserted into the carrier 40 along the opening on the upper side of the carrier 40, the seal ring 36 on the sampling end 33 slides along the inner wall of the carrier 40 with the movement of the sample collector 30, and the seal ring 36 is always in contact with the inner wall of the carrier 40; the absorption element (not shown) on the sampling end 33 squeezes against the bottom of the carrier 40, and the sample is squeezed out from the inside of the absorption element, because the seal ring 36 is always in contact with the inner wall of the carrier 40, a seal area is created at the position of the seal ring 36 in the carrier 40; when the sample collector 30 moves downward, the liquid sample in the absorption element is continuously squeezed out, and meanwhile, the sealing area also moves downward, so that the sample in the carrier 40 is pressed into the collecting chamber 22 through a through-hole 44 at the bottom of the carrier 40 to get into contact with the test paper. As a matter of fact, the absorbent element is in contact with the bottom of the carrier, so that the absorbent element is compressed, then the liquid sample collected, such as saliva sample, can flow into the bottom of the collecting chamber through the through-hole 44. The seal ring 36 is located at the upper part of the absorption element, and it is always in close contact with the side wall of the carrier to maintain a sealed state. In this way, the squeezed sample can only flow downwards. The absorption elements need to be continuously squeezed, while the seal ring has to contact the side wall of the carrier, so as to maintain a sealed state; for the above purpose, the cover body is required to seal the collecting chamber at all times, so as to ensure it does not fall off easily. One embodiment is to adopt a threaded structure, but it takes much time for the thread to rotate. The structure used in the device of the present invention is elaborated and explained in detail below.

Here, the absorption element is used to absorb a liquid sample, such as saliva, urine, sweat or other samples. The material of the absorption element can be any absorbent material, such as sponge.

Caver Body and Collecting Chamber

A cover body is used for sealing the collecting chamber to prevent the sample in the collecting chamber from leaking, as shown in FIG. 3, FIG. 6 and FIG. 7. A collecting chamber 22 is arranged on the bottle body 20, the collecting chamber 22 is used to collect a fluid sample, a testing element is arranged in the collecting chamber 22 and is used to detect the presence of the analyzed substance in the fluid sample; the collecting chamber 22 includes an opening on the upper side of the bottle body 20, a cover body 10 is used to close the opening of the collecting chamber 22, wherein the cover body 10 includes an elastic card 11 used to engage the opening of the collecting chamber 22, when the cover body 10 closes the opening of the collecting chamber 22, the elastic card 11 engages with the outer wall of the opening of the collecting chamber 22, thereby fixing the cover body 10 on the collecting chamber 22. In some embodiments, a collecting chamber comprises a carrier, and a plurality of testing elements are arranged on the carrier. As said above, the carrier is located in the collecting chamber, the collector with an absorption element is connected with the cover body, so that when the cover body closes the collecting chamber, the absorption element contacts the bottom of the carrier, then the absorption element is compressed and the liquid sample is squeezed out, thereby the liquid sample flows to the bottom of the collecting chamber and comes into contact with the testing elements at the bottom of the collecting chamber. A testing element is arranged in the groove of the carrier, the testing element includes a sample feeding area, a marker area, a detection area and an absorption area. Generally, the sample feeding area of the testing element is located at the bottom of the collecting chamber to receive a liquid sample. In this way, a part of the liquid sample flows on the testing element under a capillary force, so as to complete the test of the analyzed substance.

The elastic card 11 includes a buckle structure 12, an outer wall of the collecting chamber 22 includes a convex structure 21, and the buckle structure 12 engages the convex structure 21 when the cover body 10 closes the opening of the collecting chamber 22 as to make the cover to engage with the collecting chamber. Here, "engage" means one part is used to contact with another part together as to form a stable position. The clamping method here refers to the matching of the cover body 10 and the collecting chamber 22 in such a way as "inserting" or "piston fitting", they are fit together by clamping. Clamping is opposite to screw rotating. Screw fitting needs relative rotation so that the cover body and the collecting chamber can be fit together.

In some preferred embodiments, as shown in FIG. 12, the buckle structure 12 comprises a lower buckle surface 13 and an upper buckle surface 14, and the angle (angle 2) formed by the lower buckle surface 13 and the horizontal plane is larger than the angle (angle 1) formed by the upper buckle surface 14 and the horizontal plane, so the slope of the lower buckle surface 13 is larger than that of the upper buckle surface 14, when the cover body 10 fits with the collecting chamber 22, due to the large slope of the lower buckle surface 13, the contact between the lower buckle surface 13 and the convex structure 21 enables the elastic deformation of the elastic card 11 to be relatively easier, and there is a slow elastic deformation process between the two, therefore, a small force is needed. This can be demonstrated by the operator's feeling during separation: it can only be separated by a great force. When the cover body 10 and the collecting chamber 22 have to be separated, as the slope of the upper buckle surface 14 is small, the contact between the upper buckle surface 14 and the convex structure 21 enables the elastic deformation of the elastic card 11 to be relatively difficult. This can be demonstrated by the operator's feeling during separation: it can only be separated by a great force. Detailed descriptions are given below.

When the cover body 10 is provided with a sample collector 30, an element used to collect a fluid sample is arranged at one end of the sample collector 30, such as an absorption element, the element should be hard when it is dry; while when the element comes into contact with a liquid, such as saliva or urine, it may become soft. When the cover body 10 with an absorption element closes an opening of the collecting chamber 22, the sample collector 30 is gradually inserted in the collecting chamber 22, the absorption element contacts the squeezed surface (at the bottom of the carrier 40), with the cover body 10 being inserted, the cover body 10 gets closer to the opening of the collecting chamber 22, the absorption element is squeezed in this process so that the liquid in the absorption element is released, the cover body 10 becomes closer to the opening of the collecting chamber 22 until a convex structure 21 on the outer wall of the collecting chamber 22 contacts the lower buckle surface 13 of the buckle structure 12. In the following process, due to the elasticity of the elastic card 11, the elastic card 11 moves outward after contacting the convex structure 21 (in the direction away from the central axis of the cover body 10 until the collecting chamber 22 slides over the lower buckle surface 13 and enters the upper buckle surface 14, so that the convex structure 21 of the collecting chamber 22 contacts the upper buckle surface 14; in the following process, the elastic card 11 moves inward after contacting the convex structure 21 (in the direction of the central axis of the cover body 10) until the elastic card 11 restores to its original state, thus to complete the fitting between the cover body 10 and the collecting chamber 22, in this state, the absorption element is always in a squeezed state, and it will transfer a force separated from the collecting chamber 22 to the cover body 10 through a sample collector 30, wherein the seal ring 36 in the sample collector 30 contacts the inner wall of the carrier 40 so that partial separated force can be offset, however, in general situations, the separated force cannot be completely offset; due to the small slope of the upper buckle surface 14, a large force is needed to separate the upper buckle surface 14 from the convex structure 21, therefore, the separated force generated by the absorption element alone cannot cause deformation of the elastic card 11, on the contrary, the separated force makes the convex structure 21 of the collecting chamber 22 contacts the upper buckle surface 14 more tensely or firmly, in this case, the cover body 10 cannot be easily separated from the opening of the collecting chamber 22, and the cover body 10 will not swing on the collecting chamber 22. In this way, it can be ensured that the absorption element is always in a compressed state, and the liquid sample can be continuously released into the collecting chamber 22.

In some embodiments, in order to facilitate the convex structure 21 on the outer wall of the collecting chamber 22 to slide into the cover body 10, the lower buckle surface 13 can be a smooth surface with a certain arc; accordingly, the convex structure 21 should have a smooth surface at the best, so that when the two smooth surfaces are sliding fit to each other, frictional force can be reduced, and the cover body 10 can be fitted with the collecting chamber 22 under a small force.

In some embodiments, the convex structure 21 comprises an upper convex surface 70 and a lower convex surface 71, when the cover body 10 is fitted with the collecting chamber 22, the lower convex surface 71 of the convex structure 21 closely contacts the upper buckle surface 14 of the buckle structure 12, as shown in FIG. 12, when the upper buckle surface 14 forms a certain angle (angle 1) with the horizontal plane, the lower convex surface 71 should also form a certain angle (angle 3) with the horizontal plane, and to ensure close contact between the collecting chamber 22 and cover body 10 during fitting, the angle 3 should be equal to the angle 1; when the plane of the upper buckle surface 14 is perpendicular to the central axis of the cover body 10, the lower convex surface 71 of the corresponding convex structure 21 should also be perpendicular to the central axis of the cover body 10; in this case, the lower convex surface 71 of the collecting chamber 22 is close to the upper buckle surface 14, due to the rebound force of the elastic card 11, the cover body 10 tightly engages the collecting chamber 22, then it will become very difficult to separate the cover body 10 from the collecting chamber 22, and the elastic card 11 may break due to separation by force. In some preferred embodiments, when the cover body 10 is fitting with the collecting chamber 22, the upper convex surface 70 contacts the lower buckle surface 13 to cause deformation of the elastic 11, to make the fitting process easier, the upper convex surface 70 can be a smooth surface, or the angle formed by the upper convex surface 70 and the horizontal plane is equal to the angle (angle 2) formed by the lower buckle surface 13 and the horizontal plane. In some embodiments, the upper buckle surface 14 intersects with the lower buckle surface 13 or the extended surface of the upper buckle surface 14 intersects with the extended surface of the lower buckle surface 13, and the length of the lower buckle surface 13 is longer than the length of the upper buckle surface 14 so that the convex structure 21 of the collecting chamber 22 can easily slide into the cover body 10, and the elastic card 11 slowly deforms outwards; when the convex structure 21 slides into the upper buckle surface 14, because the upper buckle surface 14 has a relatively short distance, and the elastic card 11 has a rebounding force, the collision between the convex structure 21 and the buckle structure 12 generates a crisp sound, to remind that the cover body 10 and the collecting chamber 22 are fitted up.

In some embodiments, in order to ensure that the cover body 10 can more securely match with or fit with the collecting chamber 22, at least two elastic cards 11 or more than three of cards are arranged in the cover body 10. In some embodiments, as shown in FIG. 8-9, the cover body 10 is a half hollow sphere, and the bottle body 20 is cylindrical; wherein three elastic cards 11 are arranged in the cover body 10 in a circular array form with the center axis of the cover body 10 as the center, the elastic cards 11 are presented in an arc shape, the center of the arc is located at the central axis of the cover 10, and the elastic cards 11 will subject to elastic deformation at the side away from the center axis of the cover body 10 under the effect of the external force, so the arc-shaped elastic cards 11 can facilitate the elastic cards 11 to restore to its original state. The outer wall of the collecting chamber 22 has an annular convex structure 21, the convex structure 21 matches with three or two elastic cards 11 together, so that the cover body 10 cannot easily get away from the collecting chamber 22 when the cover body 10 is closed to the opening of the collecting chamber 22. The main purpose of the above arrangement is that if the sample collector 30 has an elastic seal ring 36, when the sample collector 30 is inserted into the collecting chamber 22, the seal ring 36 matches with the inner wall of the carrier 40 to form a sealed area, thereby making the liquid sample squeezed by the absorption element flow down to the largest extent. Because the seal ring 36 is sealed to coordinate with the inner wall of the carrier 40, it is more desirable that the cover body 10 and the collecting chamber 22 are closely fitted in the longitudinal direction, so as to avoid separation of the cover body 10 from the collecting chamber 22.

In some embodiments, a circular ring 16 is arranged on the cover body 10, and the circular ring 16 is connected with all the elastic cards 11, the circular ring 16 can enhance the strength of the connection position between the cover body 10 and the elastic cards 11, so that the elastic cards 11 is not easy to break, and meanwhile, the circular ring 16 can also wrap the opening of the collecting chamber 22, to ensure the sample in the collecting chamber 22 should not leak. Therefore, two or three elastic cards 11 may be arranged on the circular ring 16, one end of the elastic card 11 is connected to the circular ring 16, and the other end of the elastic card 11 is provided with a buckle structure 12.

In some embodiments, a limiting strip 15 is arranged on the elastic camp 11, when the cover body 10 and the collecting chamber 22 are in a fitted state, the limiting strip 15 and the buckle structure 12 can respectively limit the convex structure 21 on the outer wall of the collecting chamber 22 from the upper and lower sides, so that the cover body 10 and the bottle body 20 can be kept stable after being fitted, the limiting strip 15 extends upward into the circular ring 16 to contact the outer wall of the opening of the collecting chamber 22, thereby the upper end of the bottle body 20 can be embedded into the circular ring 16 without swinging.

The aforesaid fitting method for the cover body 10 and the collecting chamber 22 and the conventional screw rotating method for the cover body 10 and the collecting chamber 22 both have the advantages of easy operation, squeezing the absorption element, and improving testing efficiency, but relatively speaking, in the repeated testing process, the screw rotating method is much more complicated than the technical solution provided by the present invention, and it is also difficult to operate. The purpose of the detection device of the present invention is to quickly obtain the preliminary detection result, and "fast" and "convenient" are the primary requirements that the detection device of the present invention intends to meet.

In some embodiments, a guide structure is provided in the cover body 10, and the guide structure is located between the adjacent elastic cards 11, because at least two elastic cards 11 are arranged in the cover body 10, correspondingly, at least two guide structures are arranged, the guide structure includes a guide blade 17, the guide blade 17 is connected to the bottom of the cover body 10 and the circular ring 16, and rounded corners 18 are arranged at the edges; the guide structure has a guide effect in closing the cover body 10 and the collecting chamber 22, it is not necessary to align the opening of the collecting chamber 22 with the buckle area formed by the inner elastic card 11 of the cover body 10 when using to easily achieve fitting between the cover body 10 and the collecting chamber 22; because when the opening of the collecting chamber 22 is not aligned with the buckle area formed by the inner elastic card 11 of the cover body 10, the upper end of the bottle body 20 comes into contact with the blade, it may enter the fitting area under the guidance of the round corner 18 to facilitate accurate operation, a convex support 19 is arranged on the guide blade 17, the height of the lower end of the convex support 19 is the same as that of the limiting strip 15, and this can limit the position of the convex structure 21, the upper end of the convex support 19 extends into the circular ring 16 as the limiting strip 15, to contact the opening position of the bottle body 20, so that the cover body 10 cannot swing on the bottle body 20; in addition, after the guide blade 17 is connected to the bottom part and the circular ring 16 of the cover body 10, the overall strength of the cover body 10 is strengthened to some extent, as shown in FIG. 8, there are six guide blades and the guide blades 17 are arranged respectively between the adjacent elastic cards 11 in a circular array. The guide structure is particularly convenient and effective when repeated tests are required. When using, the guide structure can introduce the opening of the collecting chamber 22 into the elastic card 11 without intentionally aligning the position.

In some embodiments, as shown in FIG. 10, after the half hollow spherical cover body 10 and the cylindrical bottle body 20 are fitted together, the detection device is made into a mushroom shape as a whole, cute and artistic, and the device can remove the fear of the subject, more easily to be accepted, in some other embodiments, as shown in FIG. 11, the cover body 10 is cylindrical, as compared with a mushroom-shaped detection device, this detection device takes up less space and is convenient to carry.

In some embodiments, a hollow connection portion 80 is arranged on the cover body 10, the hollow connection portion 80 is used to connect a sample collector 30, the cross connector 34 can be inserted into the hollow connection portion 80 by pressing the pressing platform 37 with the index and middle fingers, thus to complete the connection between the cover body 10 and the sample collector 30. When the cover body 10 and the collecting chamber 22 are in a fitted state, the absorption element of the sample collector 30 is in a compressed state, and it will transfer a force separated from the collecting chamber 22 to the cover body 10, but because the force produced by the absorption element when it is compressed is small, far less than the force required to separate the cover body 10 from the collecting chamber 22, the buckle structure 12 and the convex structure 21 cannot be separated.

The above are only specific embodiments of the invention, but the protection scope of the invention is not limited to this, any changes or replacements that come into mind without creative work should be included in the scope of protection of the invention. Therefore, the protection scope of the invention is subjected to the protection scope defined by the Claims.

In the absence of any element or limitation specifically disclosed herein, the invention shown and described herein may be achieved. Terms and expressions used are used as descriptive terms and not as a limitation, it's not intended to exclude any equivalent of characteristics or a part of them shown and described in use of these terms and expressions, and it should be recognized that all modifications are feasible within the scope of the present invention. It should therefore be understood that, although the present invention has been specifically disclosed through various embodiments and optional characteristics, modifications and variations of concepts described herein may be employed by ordinary technical personnel skilled in the art, and these modifications and variations are considered to fall within the scope of the present invention defined by the attached claims.

The content of articles, patents, patent applications and all other documents and electronically available information described or documented herein is to some extent incorporated in the full text for reference, as if each individual publication is specifically and individually pointed out for reference. The applicant reserves the right to incorporate any and all materials and information from any such articles, patents, patent applications or other documents into the present application.

The invention claimed is:

1. A detection device comprising:
   a collecting chamber configured to collect a fluid sample, the collecting chamber including an opening;
   a testing element, arranged in the collecting chamber, configured to test the presence of an analyzed substance in the fluid sample;
   a cover body configured to close the opening of the collecting chamber; and
   a sample collector, arranged on the cover body and having an absorption element;
   wherein the cover body includes an elastic card configured to engage with the opening of the collecting chamber, when the cover body closes the opening of the collecting chamber, the elastic card engages an outer wall of the opening of the collecting chamber, thereby fixing the cover body on the collecting chamber in a clamping way, the sample collector is inserted into the collecting chamber, and the absorption element is compressed such that the fluid sample is squeezed out to flow to a bottom of the collecting chamber and to come into contact with the testing element;
   wherein the elastic card includes a buckle structure, an outer wall of the collecting chamber includes a convex structure, and the buckle structure engages the convex structure when the cover body closes the opening of the collecting chamber;
   wherein a limiting strip is arranged on the elastic card, when the cover body and the collecting chamber are in a fitted state, the limiting strip and the buckle structure respectively limit the convex structure on the outer wall of the collecting chamber from upper and lower sides, so that the cover body and the collecting chamber are able to be kept stable after being fitted.

2. The detection device of claim 1, wherein the buckle structure comprises a lower buckle surface and an upper buckle surface, and an angle formed by the lower buckle surface and a horizontal plane is larger than an angle that formed by the upper buckle surface and the horizontal plane.

3. The detection device of claim 2, wherein the lower buckle surface is a smooth surface, the convex structure on the collecting chamber includes an upper convex surface and a lower convex surface, wherein the upper convex surface and the lower buckle surface contacts to drive contacting between the lower convex surface and the upper buckle surface.

4. The detection device of claim 3, wherein a slope of the upper convex surface is smaller than that of the lower convex surface so that the upper convex surface can contact the lower buckle surface of the buckle structure of the elastic card in a sliding way.

5. The detection device of claim 1, wherein at least two elastic cards are arranged inside the cover body.

6. The detection device of claim 5, wherein a circular ring is arranged in the cover body and the circular ring is connected with all elastic cards.

7. The detection device of claim 6, wherein the limiting strip extends into the circular ring.

8. The detection device of claim 1, wherein the elastic card is arc-shaped.

9. The detection device of claim 7, wherein a guide structure is arranged in the cover body, the guide structure is adjacent to the elastic card, and there are at least two guide structures.

10. The detection device of claim 9, wherein the guide structure comprises a guide blade, the guide blade connects a bottom part of the cover body and the circular ring, and a round corner is arranged at the edge of the guide structure.

11. The detection device of claim 10, wherein a convex support is arranged on the guide blade, and the height of a lower end of the convex support is the same as that of a lower end of the limiting strip.

12. The detection device of claim 1, further comprising a carrier, a plurality of card slots for the testing element being arranged on the carrier, wherein the carrier is located in the collecting chamber, and the carrier is provided with a cavity, and the carrier also has a bottom part and there is no vent hole at the bottom part of the carrier.

13. The detection device of claim 12, wherein the sample collector is configured to be inserted in the cavity inside the carrier and contact the bottom part of the carrier.

14. The detection device of claim 13, wherein the fluid sample is saliva.

15. The detection device of claim 14, wherein the sample collector comprises a sampling element, the sampling element is connected with the cover body through a sampling rod, an elastic seal ring is arranged above the sampling element, and the elastic seal ring is sealed with an inner chamber wall when the sampling element is inserted in an inner chamber of the carrier.

16. The detection device of claim 12, wherein a blank area is reserved on the carrier, and no testing element is arranged in the blank area; a sample area for another testing is reserved at a bottom part of the collecting chamber, and the sample area is located at a lower part of the blank area.

17. The detection device of claim 16, wherein the cavity is arranged on the carrier and the cavity is a part of the sample area.

18. The detection device of claim 16, wherein the sample area adopts a cavity structure, a sampling hole is arranged on the cavity structure, the fluid sample in the cavity can be absorbed through the sampling hole for the another testing.

19. The detection device of claim 12, wherein a blank area is reserved on the carrier, and no testing element is arranged in the blank area; wherein the blank area is located at a fixed position in the collecting chamber when assembly of the collecting chamber and the carrier is completed.

\* \* \* \* \*